(12) United States Patent
Ishibiki

(10) Patent No.: US 6,821,244 B2
(45) Date of Patent: Nov. 23, 2004

(54) ENDOSCOPE AND MANUFACTURING METHOD THEREFOR

(75) Inventor: Kouta Ishibiki, Hachioji (JP)

(73) Assignee: Olympus Corporation, Tokyo (JP)

(*) Notice: Subject to any disclaimer, the term of this patent is extended or adjusted under 35 U.S.C. 154(b) by 67 days.

(21) Appl. No.: 10/183,077

(22) Filed: Jun. 27, 2002

(65) Prior Publication Data

US 2003/0013940 A1 Jan. 16, 2003

(30) Foreign Application Priority Data

Jun. 27, 2001 (JP) .................................. 2001-195131

(51) Int. Cl.⁷ .................................................. A61B 1/00
(52) U.S. Cl. .................. 600/139; 600/133; 600/140
(58) Field of Search ........................... 600/133, 139, 600/140, 143, 151, 130, 920

(56) References Cited

U.S. PATENT DOCUMENTS 4,899,787 A  2/1990  Ouchi et al.
6,514,198 B2 *  2/2003  Ishibiki ..................... 600/133

FOREIGN PATENT DOCUMENTS

JP          10-276968        10/1998

* cited by examiner

Primary Examiner—Beverly M. Flanagan
(74) Attorney, Agent, or Firm—Scully, Scott, Murphy & Presser

(57) ABSTRACT

An endoscope is provided with a pliable tube composed of an integument layer formed from a resin and a metal tube integrally fitted into this integument layer in an insertion portion. The inner diameter dimension of the pliable tube at ambient temperature after application of the thermal load of the high-pressure steam sterilization step is larger than the inner diameter dimension at ambient temperature before application of the thermal load.

10 Claims, 8 Drawing Sheets

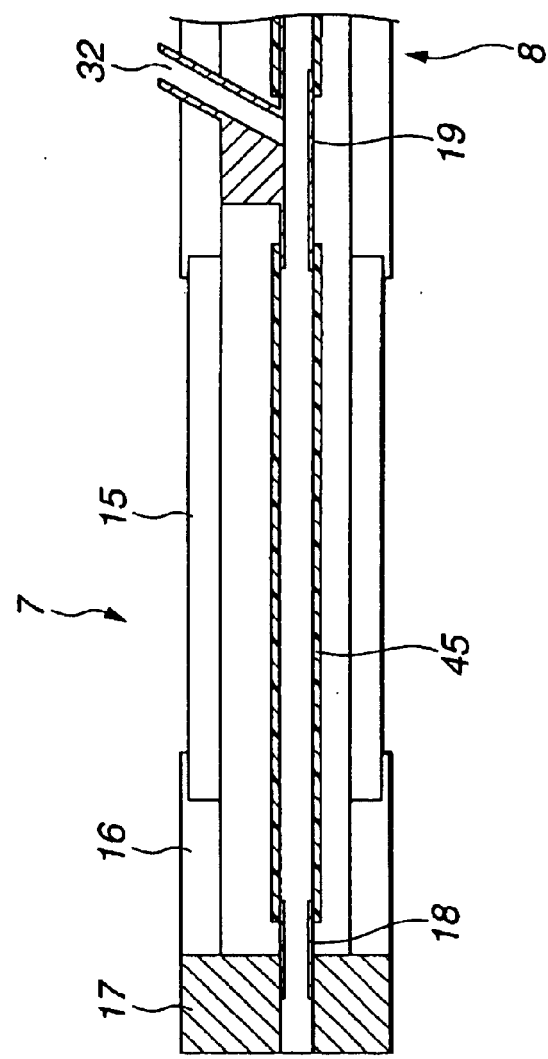
FIG.4
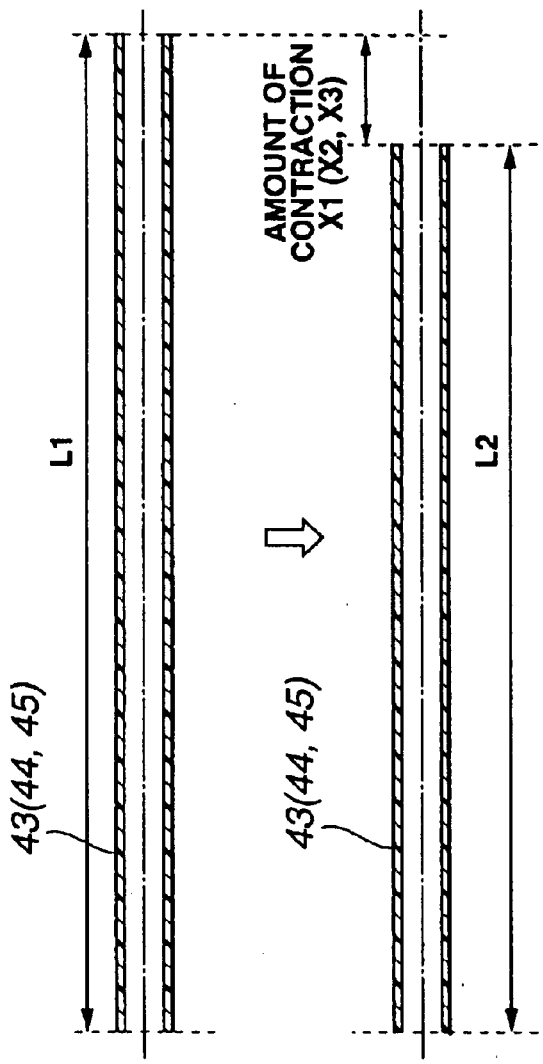
FIG.5A
FIG.5B

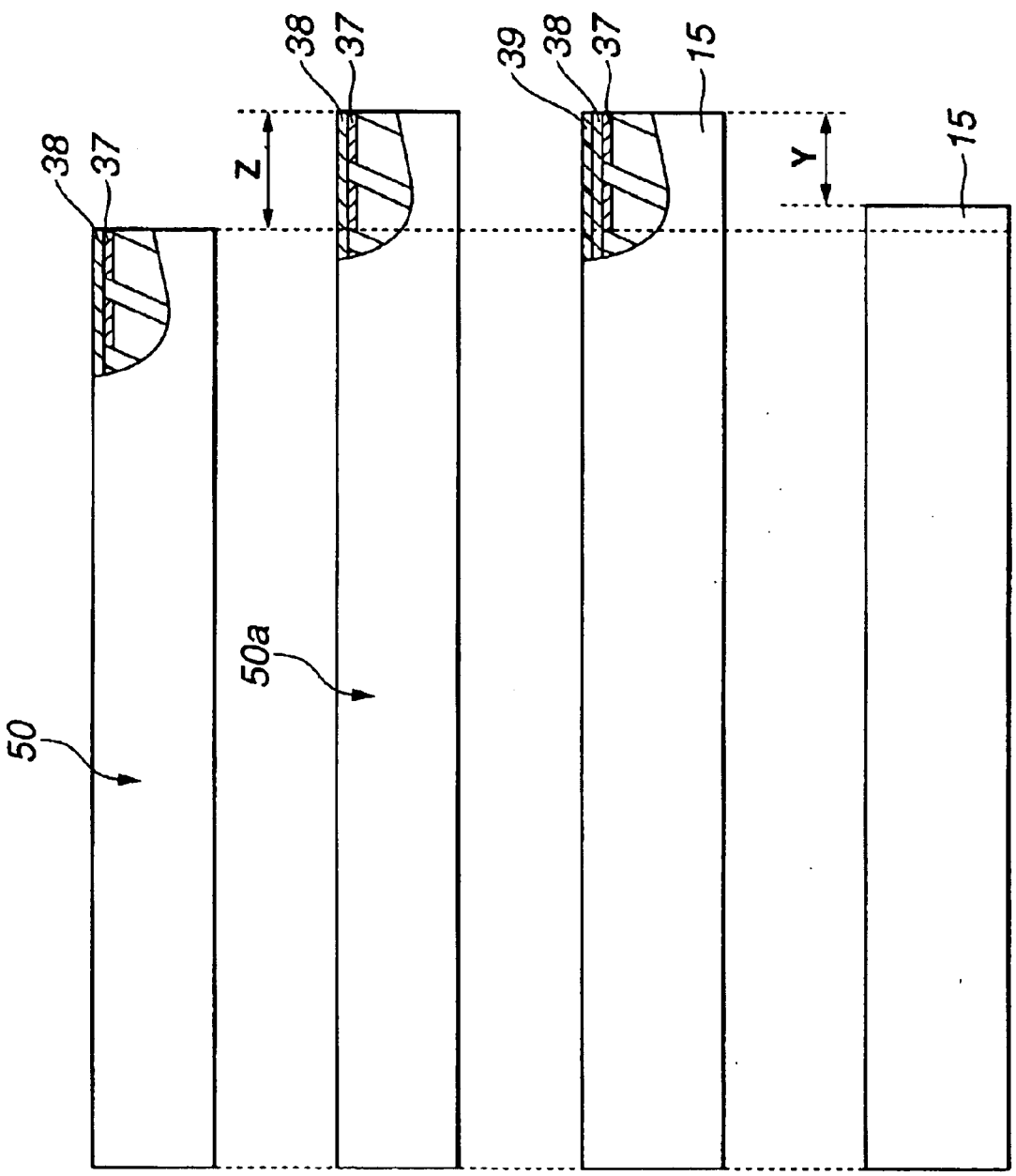

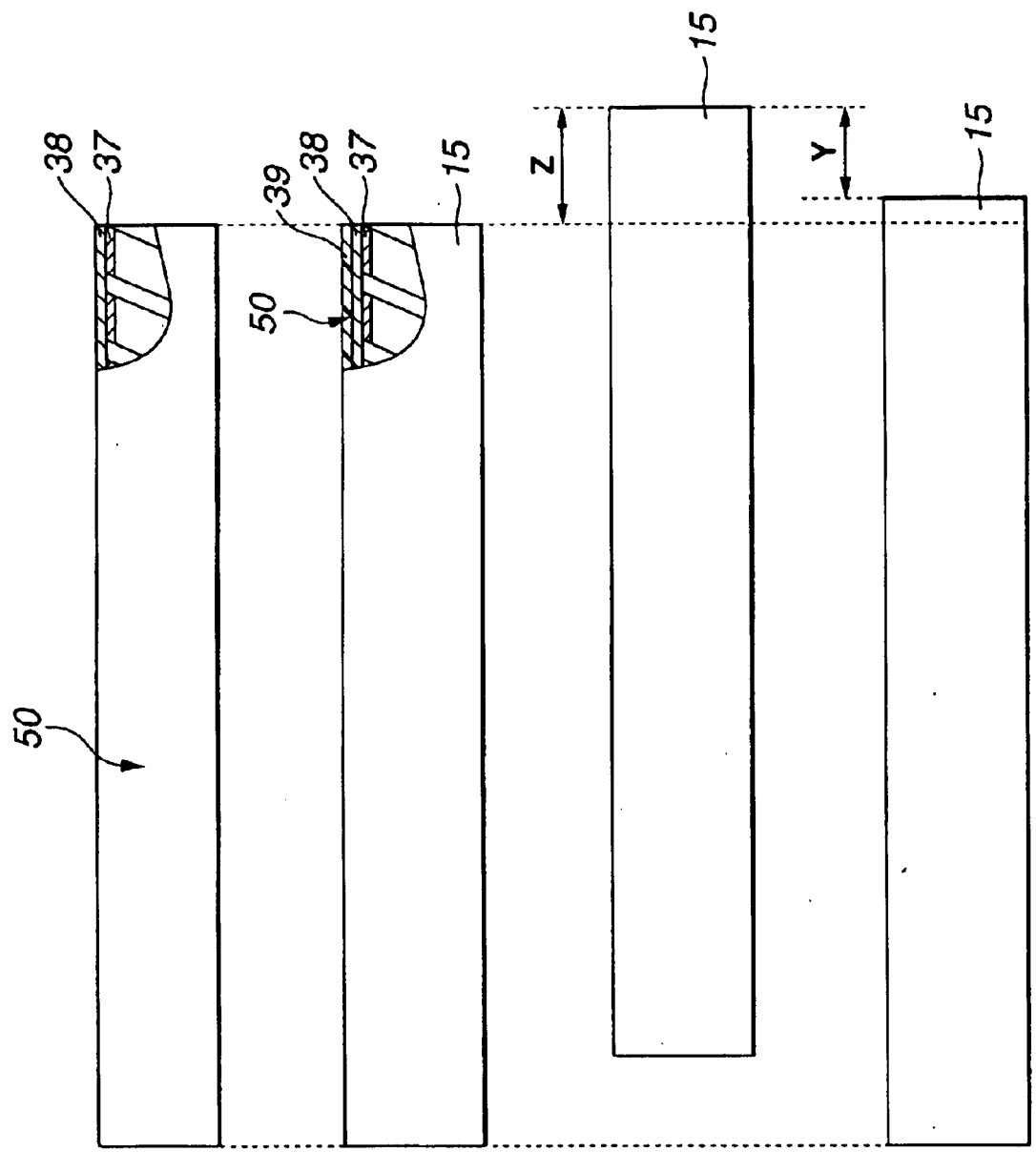

ENDOSCOPE AND MANUFACTURING METHOD THEREFOR

This application claims benefit of Japanese Application No. 2001-195131 filed on Jun. 27, 2001, the contents of which are incorporated by this reference.

BACKGROUND OF THE INVENTION

1. Field of the Invention

The present invention relates to an endoscope provided with a pliable tube composed of an integument layer formed from a resin and a metal tube integrally fitted into this integument layer in an insertion portion, and a manufacturing method therefor.

2. Description of Related Art

Hitherto, medical endoscopes have been used widely, wherein organs in body cavities, etc., can be observed by inserting slender insertion portions in the body cavities and, if necessary, various therapeutic treatments can be performed using endo-therapy products inserted through endo-therapy product channels.

In particular, regarding the endoscope used in a medical field, by inserting the insertion portion in the body cavity, observation of organs, etc., is performed and various therapies and treatments are performed using endo-therapy products inserted through the endo-therapy product channel of the endoscope. Consequently, when an endoscope and endo-therapy product used once have been reused for other patients, it has been necessary to perform cleaning and disinfection after an inspection and treatment has been completed for reasons of necessity to prevent cross infection between patients through the endoscope and endo-therapy product.

In recent years, inexpensive autoclave sterilization (high-pressure steam sterilization) has become the mainstream of the disinfection and sterilization treatments of medical equipment, wherein no complicated operation attends, it is possible to use immediately after sterilization, and a running cost is low.

However, when the step of high-pressure steam sterilization was performed repeatedly over the long term, the resin forming the integument of the pliable tube became in the condition of being likely to deform due to the thermal load, and sometimes, it was feared that the inner diameter of the pliable tube shrank during the pressurizing step in the high-pressure steam sterilization step.

When the integument formed into nearly the shape of a tube or the helical tube and mesh-shaped tube fitted into this integument are formed while being applied with a stress in the direction of diameter increase, that is, while being pulled in the direction of diameter increase, during manufacture, the inner diameter of the pliable tube may contract due to contraction of the diameter of the helical tube or mesh-shaped tube. If the inner diameter dimension of the pliable tube contract, it is feared that the built-in light guide, electric cables, and pipeline tubes will be oppressed and inconvenience, for example, breakage, will be brought about.

The present invention was made in consideration of the aforementioned circumstances. Accordingly, it is an object of the present invention to provide an endoscope in which even when high-pressure steam sterilization is performed repeatedly, occurrence of inconvenience of built-in materials due to the inner diameter of the pliable tube being changed in the direction of contraction is prevented, that is, the inner diameter dimension of the pliable tube remains in the condition as it is, or the diameter becomes in the condition of being increased.

SUMMARY OF THE INVENTION

An endoscope according to the present invention is an endoscope provided with a pliable tube composed of an integument layer formed from a resin and a metal tube integrally fitted into this integument layer in an insertion portion, and the inner diameter dimension of the aforementioned pliable tube at ambient temperature after application of the thermal load of the high-pressure steam sterilization step is larger than the inner diameter dimension at ambient temperature before application of the thermal load.

According to this configuration, a force in the direction of diameter increase is always exerted during high-pressure steam sterilization and, therefore, it can be prevented with reliability that the inner diameter of the pliable tube becomes equivalent to or less than the inner diameter dimension at ambient temperature. The above and other objects, features and advantages of the invention will become more clearly understood from the following description referring to the accompanying drawings.

BRIEF DESCRIPTION OF THE DRAWINGS

FIG. 4 is a diagram for explaining the installment conditions in an insertion portion of a tube element according to an embodiment of the present invention.

FIG. 5A and FIG. 5B are diagrams for explaining the amount of contraction of a tube element according to an embodiment of the present invention.

FIG. 5A is a diagram showing the condition of the tube in the initial condition, and FIG. 5B is a diagram showing the condition of the tube after high-pressure steam sterilization.

FIG. 6A is a diagram showing the condition of the pliable tube in the initial condition, and FIG. 6B is a diagram showing the condition of the pliable tube after high-pressure steam sterilization.

FIG. 7A, FIG. 7B, FIG. 7C, and FIG. 7D are diagrams for explaining a formation step of a pliable tube according to an embodiment of the present invention.

FIG. 7A is a diagram showing an assembly in which a helical tube and a mesh-shaped tube in the natural length conditions are combined. FIG. 7B is a diagram showing the assembly extended by a predetermined length, FIG. 7C is a diagram showing the pliable tube formed by applying a covering of integument layer to the extended assembly, and FIG. 7D is a diagram showing the pliable tube in the condition of being shrunken after high-pressure steam sterilization.

FIG. 8A, FIG. 8B, FIG. 8C, and FIG. 8D are diagrams for explaining another formation step of a pliable tube according to an embodiment of the present invention.

FIG. 8A is a diagram showing an assembly in which a helical tube and a mesh-shaped tube in the natural length conditions are combined, FIG. 8B is a diagram showing the assembly in the condition of being provided with an integument layer, FIG. 8C is a diagram showing the pliable tube formed by extending the assembly covered with the integument layer, and FIG. 8D is a diagram showing the pliable tube in the condition of being shrunken after high-pressure steam sterilization.

FIG. 9A is a sectional view explaining a helical tube and a mesh-shaped tube in the natural length conditions. FIG. 9B is a sectional view explaining the pliable tube in the pliable tube formation conditions.

FIG. 10A is a sectional view explaining a helical tube in the natural length conditions. FIG. 10B is a sectional view explaining the pliable tube in the pliable tube formation conditions.

DETAILED DESCRIPTION OF PREFERRED EMBODIMENTS

The embodiments according to the present invention will be described below with reference to the drawings.

The embodiments regarding endoscopes, in which inconvenience brought about due to contraction of a tube element built in an insertion portion during high-pressure steam sterilization is prevented, will be described.

Figure 1:
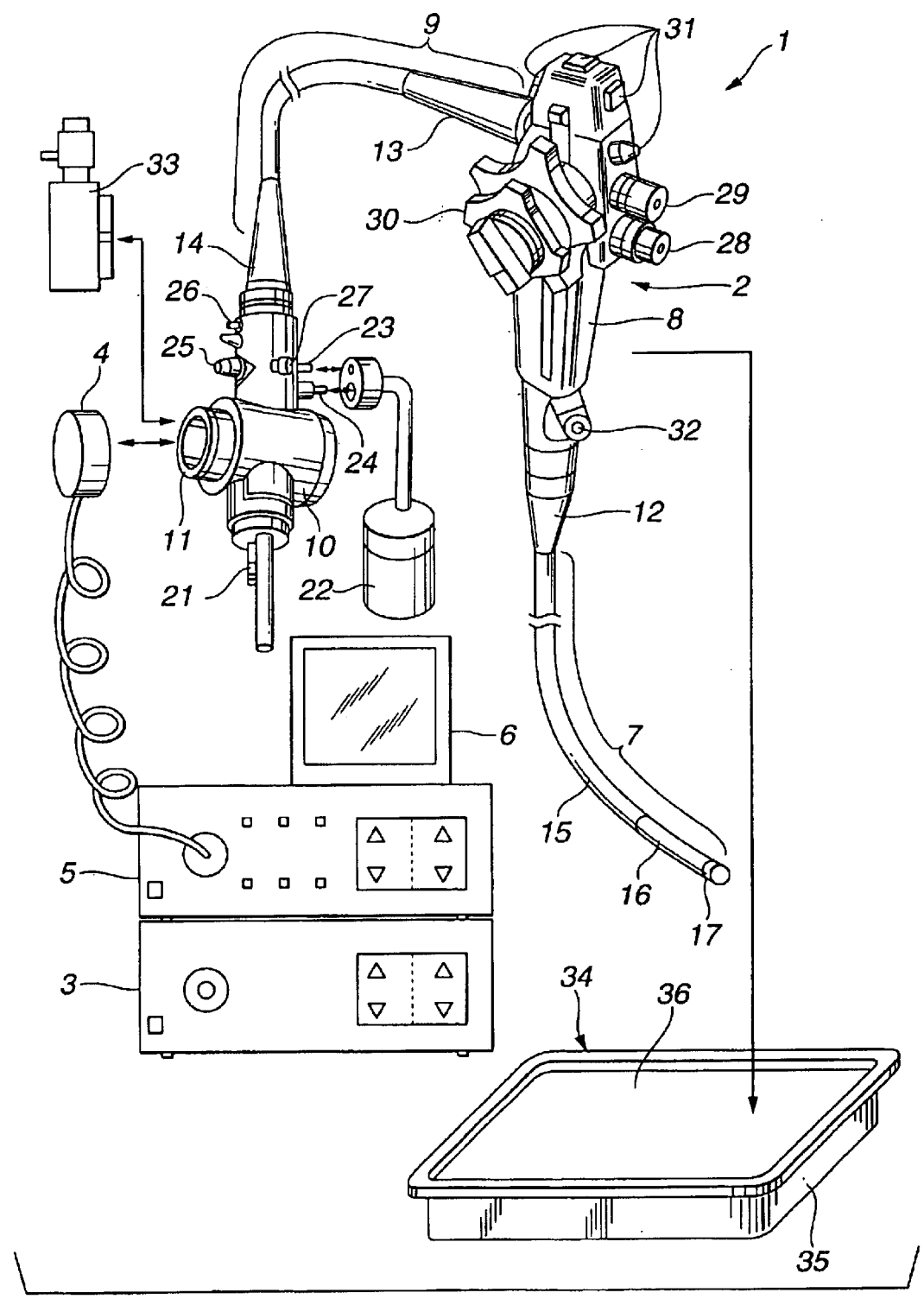
FIG. 1 is a diagram for explaining the configuration of an endoscope apparatus according to an embodiment of the present invention.
Figure 2:
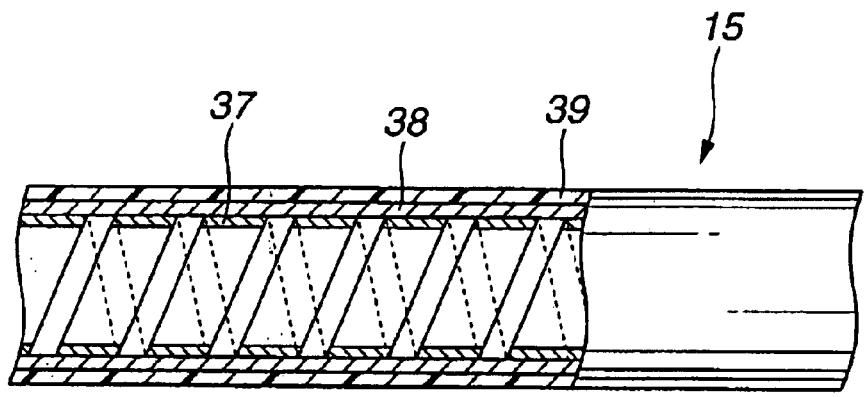
FIG. 2 is a partial sectional view for explaining the configuration of a pliable tube according to an embodiment of the present invention.
Figure 3:
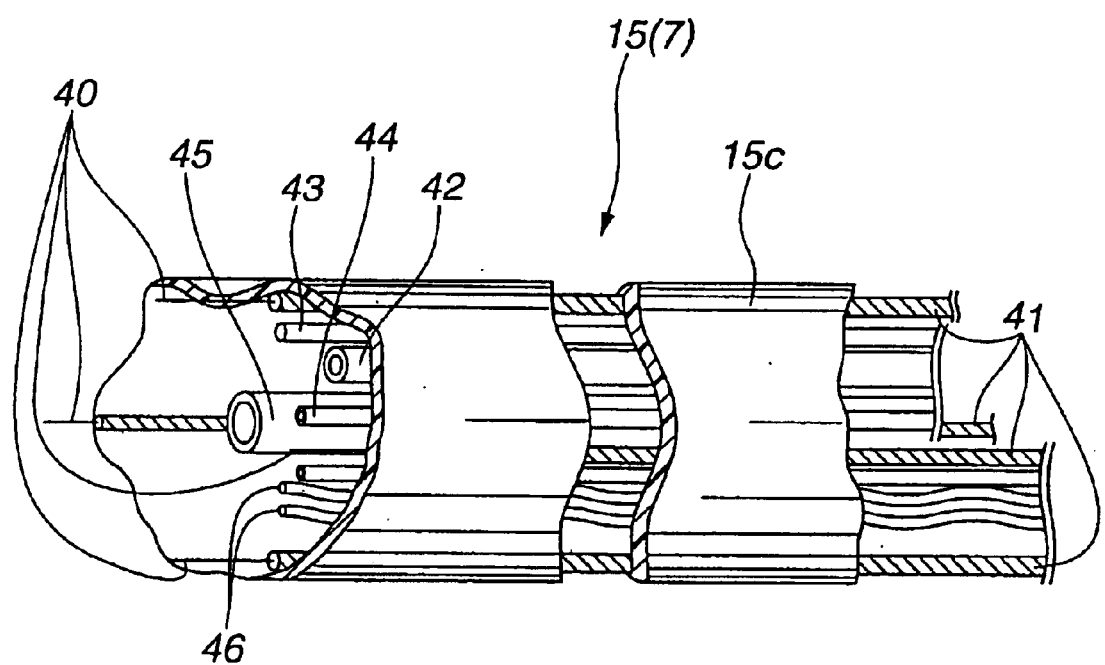
FIG. 3 is a diagram for explaining built-in materials inserted through a pliable tube according to an embodiment of the present invention.

FIG. 1 to FIG. 8D are diagrams for explaining endoscopes according to those embodiments. FIG. 1 is a diagram for explaining the configuration of an endoscope apparatus. FIG. 2 is a partial sectional view for explaining the configuration of a pliable tube. FIG. 3 is a diagram for explaining built-in materials inserted through a pliable tube. FIG. 4 is a diagram for explaining the installment conditions in an insertion portion of a tube element. FIG. 5A and FIG. 5B are diagrams for explaining the amount of contraction of a tube element. FIG. 6A and FIG. 6B are diagrams for explaining the amount of contraction of a pliable tube. FIG. 7A to FIG. 7D are diagrams for explaining a formation step of a pliable tube. FIG. 8A to FIG. 8D are diagrams for explaining another formation step of a pliable tube.

FIG. 7A is a diagram showing an assembly in which a helical tube and a mesh-shaped tube in the natural length conditions are combined. FIG. 7B is a diagram showing the assembly extended by a predetermined length. FIG. 7C is a diagram showing the pliable tube formed by applying a covering of integument layer to the extended assembly. FIG. 7D is a diagram showing the pliable tube in the condition of being shrunken after high-pressure steam sterilization. FIG. 8A is a diagram showing an assembly in which a helical tube and a mesh-shaped tube in the natural length conditions are combined. FIG. 8B is a diagram showing the assembly in the condition of being provided with an integument layer. FIG. 8C is a diagram showing the pliable tube formed by extending the assembly covered with the integument layer. FIG. 8D is a diagram showing the pliable tube in the condition of being shrunken after high-pressure steam sterilization.

As shown in FIG. 1, an endoscope apparatus 1 according to the present embodiment is primarily composed of an electronic endoscope (hereafter simply referred to as endoscope) 2 provided with an image pickup device, light equipment 3 for supplying illumination light, a video processor 5 which controls the image pickup device and which treats signals attained from the aforementioned image pickup device, and a monitor 6 connected to this video processor 5. Reference numeral 34 denotes a container case for sterilization, described later, which contains this endoscope 2.

The aforementioned endoscope 2 is composed of a slender insertion portion 7 having pliability, a control portion 8 connected to the base end portion of this insertion portion 7, and a universal cord 9 which has pliability and which extends from the side of this control portion 8.

A connector 10, which is freely attached to or detached from the aforementioned light equipment 3, is installed at the end portion of the aforementioned universal cord 9. By connecting this connector 10 to the light equipment 3, illumination light from a lamp, although not shown in the drawing, provided on the light equipment 3 is transmitted through a light guide, although not shown in the drawing, of the endoscope 2 and, therefore, radiates an observation section.

A folding-preventing member 12 of the insertion portion, which is composed of an elastic member and which is for preventing tight turning, is installed at the joint portion of the aforementioned insertion portion 7 and the control portion 8. Likewise, a folding-preventing member 13 of the control portion is installed at the joint portion of the aforementioned control portion 8 and the universal cord 9. Likewise, a folding-preventing member 14 of the connector is installed at the joint portion of the universal cord 9 and the connector 10.

The slender insertion portion 7 having pliability of the aforementioned endoscope 2 is configured to install succeedingly a hard tip portion 17 provided with, for example, an observation window, illumination window, etc., although not shown in the drawing, at the tip surface, a curved portion 16 in which a plurality of bending parts are connected succeedingly and which is curved freely, and a pliable tube 15 having pliability in that order from the tip side. The aforementioned curved portion 16 is curved by operating appropriately a curve control knob 30 installed on the control portion 8, and the tip surface of the tip portion 17 provided with the observation window, etc., can be faced a desired direction.

The aforementioned control portion 8 is provided with a gas supply and water supply operation button 28, a suction operation button 29, a plurality of remote switches 31, . . . , and 31 for remotely controlling the aforementioned video processor 5, and an endo-therapy product insertion hole 32 communicating with an endo-therapy product channel installed in the insertion portion of the endoscope 2 in addition to the aforementioned curve control knob 30. The gas supply and water supply operation button 28 is a button for performing a gas supply operation or water supply operation when a cleaning liquid or gas is ejected toward the aforementioned observation window from a gas supply and water supply nozzle, although not shown in the drawing, installed on the tip surface. The suction operation button 29 is a button for performing a suction operation through a suction hole, although not shown in the drawing, installed on the tip surface.

An electric connector portion 11 is installed on the side portion of the aforementioned connector 10. A signal connector 4 of a signal cord connected to the aforementioned video processor 5 is connected to the electric connector portion 11 while being free to attach or detach. By connecting this signal connector 4 to the video processor 5, the image pickup device of the endoscope 2 is controlled and, in addition, by producing image signals from electric signals transmitted from this image pickup device, an endoscope observation image is displayed on the screen of the aforementioned monitor 6. A vent hole, although not shown in the drawing, communicating the inside and outside of the endoscope 2 is installed in the electric connector portion 11. Consequently, the electric connector portion 11 of the endoscope 2 is configured in order that a waterproof cap 33 with a pressure control valve (hereafter abbreviated as waterproof cap) provided with the pressure control valve (not shown in the drawing) for blocking the aforementioned vent hole is free to attach or detach.

This connector 10 is provided with a gas supply base 21 connected to a gas supply source, although not shown in the drawing, built in the light equipment 3 while being free to attach or detach, a base 23 for pressurizing a water supply tank 22 and a liquid supply base 24 connected to the water supply tank, which is a liquid supply tank, while being free to attach or detach, a suction base 25 connected to a suction source, although not shown in the drawing, in order to perform suction from the aforementioned suction hole, and an injection base 26 connected to a water supply device, although not shown in the drawing, in order to perform supply of water.

Furthermore, this connector 10 is provided with an earth terminal base 27 in order to return a leakage current to a high-frequency treatment apparatus, although not shown in the drawing, when the high-frequency leakage current is generated in the endoscope 2 during performance of the high-frequency treatment, etc.

The aforementioned endoscope 2 is configured to be capable of undergoing high-pressure steam sterilization after being used for an observation or a treatment and being cleaned. When this endoscope 2 is subjected to the high-pressure steam sterilization, the aforementioned waterproof cap 33 is fitted to the electric connector portion 11.

When the aforementioned endoscope 2 is subjected to the high-pressure steam sterilization, this endoscope 2 is contained in a container case 34 for sterilization. This container case 34 for sterilization is composed of a tray 35, which is a case body, and a cover member 36. This tray 35 is provided with a regulation member corresponding to the shape of the endoscope, although not shown in the drawing, in order that each of the insertion portion 7, control portion 8, universal cord 9, connector 10, etc., of the endoscope 2 is located at a predetermined position.

A plurality of vent holes for introducing high-pressure steam are formed in these tray 35 and cover member 36.

As shown in FIG. 2, a helical tube 37 which constitutes the innermost layer and which is formed by helically winding a thin band-shaped piece of metal, a mesh-shaped tube 38, and a integument layer 39 integrally installed covering the outer perimeter of this mesh-shaped tube 38 are laminated and, therefore, the aforementioned pliable tube 15 is formed. The mesh-shaped tube 38 is formed into the shape of a tube by knitting a thin metal wire, knitting a thin non-metal wire, or knitting them, each being installed covering the outer perimeter of this helical tube 37. The aforementioned integument layer 39 is formed from a resin material, for example, a thermoplastic elastomer.

As shown in FIG. 3, a plurality of slender built-in materials are inserted through the insertion portion 7 including the aforementioned pliable tube 15. These built-in materials includes curve control wires 40 which are made of a metal and which are moved forward or backward by the operation of the aforementioned curve control knob 30 in order to bring about curving action of the aforementioned curved portion 16 in, for example, the vertical or horizontal direction, a wire-covered coil 41 which is made of a metal and which covers these curve control wires 40 in the condition of being inserted movably, a light guide 42 made of an optical fiber bundle for supplying illumination light, a gas supply tube 43 and a water supply tube 44 which are tube elements for transporting fluids and which are formed from PTFE, etc., a channel tube for inserting a endo-therapy product (hereafter referred to as endo-therapy product tube) 45 which serves as a channel for inserting the endo-therapy product and also serves as a suction pipeline of the fluids, a plurality of electric cables 46, and the like.

The aforementioned gas supply tube 43, water supply tube 44, and endo-therapy product tube 45 are fixed to, for example, connection pipes 18 described below, which are connection portions installed individually at the control portion 8 and the tip portion 17 connected succeedingly to both ends of the insertion portion 7.

As shown in FIG. 4, for example, one end of the aforementioned endo-therapy product tube 45 is connected and is fixed to the connection pipe 18 fixed to the tip portion 17. On the other hand, the other end of the aforementioned endo-therapy product tube 45 is connected and is fixed to a branch member 19 having the aforementioned endo-therapy product insertion hole 32.

The aforementioned branch member 19 is fixed integrally to a base, although not shown in the drawing, installed at the base end of the pliable tube 15 with the control portion 8 therebetween. The aforementioned tip portion 17 is fixed integrally to a base, although not shown in the drawing, installed at the tip of the pliable tube 15 with the aforementioned curved portion 16 therebetween.

Under this fixing condition, for example, when the aforementioned endo-therapy product tube 45 contracts, a force which brings about the curving action of the aforementioned curved portion 16 in any direction is effected through the tip portion 17. According to this, inconvenience occurs in that the curved portion 16 is curved in an unintended direction, the amount of control force required for the curving operation is increased, and the like.

FIG. 5A is a diagram showing the condition of a tube in the initial condition, and FIG. 5B is a diagram showing the condition of the tube after high-pressure steam sterilization. As shown in FIG. 5B, when the endoscope 2 is subjected to high-pressure steam sterilization repeatedly, the lengths of the aforementioned gas supply tube 43, water supply tube 44, and endo-therapy product tube 45 become L2 because contraction occurs individually in the longitudinal direction compared with the length L1 in the initial condition due to thermal loads during this high-pressure steam sterilization. These amounts of contraction of the gas supply tube 43, water supply tube 44, and endo-therapy product tube 45 are X1, X2, and X3, respectively.

The aforementioned amounts of contraction are brought about because in manufacture, the aforementioned tubes 43, 44, and 45 are molded under the condition of being pulled during molding, for example, extruding, and because these tubes 43, 44, and 45 become in the condition of being able to deform by thermal loads and, therefore, stresses are released.

In consideration of these, regarding the pliable tube 15 according to the present embodiment, the amount of contraction when a thermal load is applied during the step of high-pressure steam sterilization is set larger than the amount of contraction of the aforementioned gas supply tube 43, water supply tube 44, and endo-therapy product tube 45.

Figure 6A:
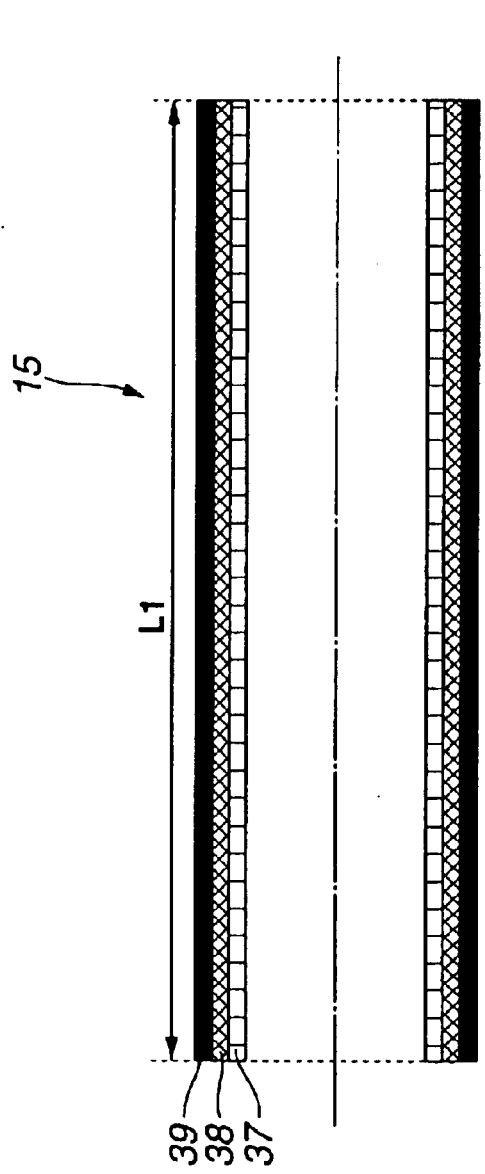
FIG. 6A and FIG. 6B are diagrams for explaining the amount of contraction of a pliable tube according to an embodiment of the present invention.
Figure 6B:
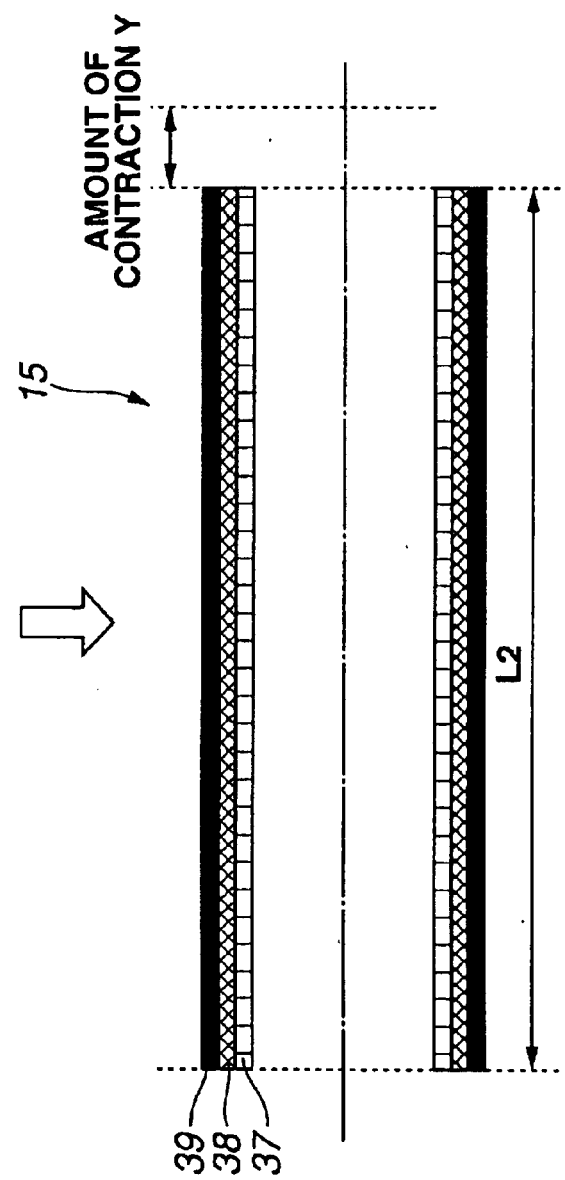

Herein, the length of the pliable tube 15 is assumed to change from the length L1 in the initial condition to the length L2 after the high-pressure steam sterilization, and the amount of contraction of the pliable tube 15 due to the thermal load of the high-pressure steam sterilization is assumed to be Y as shown in FIG. 6B. Then, the following relationships are set between this Y and the aforementioned X1, X2, and X3.

$$Y \geq X1, Y \geq X2, \text{ and } Y \geq X3$$

In order to set these relationships between the aforementioned pliable tube 15 and the tubes 43, 44, and 45, a thermal load of the high-pressure steam sterilization is applied to the aforementioned tubes 43, 44, and 45, and amounts of contraction X1, X2, and X3 are measured and determined by calculation in advance. Subsequently, the pliable tube 15 is formed in order that the amount of contraction Y of the aforementioned pliable tube 15 becomes greater than the amounts of contraction X1, X2, and X3 of those tubes 43, 44, and 45.

Herein, the formation step of the pliable tube 15 will be described.

The resin material for forming the integument layer 39 of the aforementioned pliable tube 15 is selected in consideration of usage conditions, for example, durability, insertion property into the body cavity, etc., during use, and resistance against agents, etc., used for cleaning and disinfection. In the present embodiment, when the resin material for forming the aforementioned integument layer 39 is selected, in addition to the aforementioned usage conditions, the one having such a thermal deformation temperature that deformation is brought about by a thermal load during high-pressure steam sterilization is selected. Herein, a temperature, at which a resin can be deformed by a thermal load during high-pressure steam sterilization, is defined as a thermal deformation temperature H for the sake of convenience.

When the resin material for the integument layer 39 is selected, since the upper limit of the temperature during a general high-pressure steam sterilization step is on the order of 140° C., the integument layer 39 is formed from, for example, the one primarily containing ester-based thermoplastic elastomer which is a resin material satisfying $H \leq 140°$ C.

On the other hand, regarding the helical tube 37 and the mesh-shaped tube 38 constituting the aforementioned pliable tube 15, assembling is performed in the pliable tube formation conditions in which these helical tube 37 and mesh-shaped tube 38 are brought about in the condition of being extended compared with being in the natural length conditions.

That is, as shown in FIG. 7A, an assembly 50 is formed in which the helical tube 37 and mesh-shaped tube 38 are combined. As shown in FIG. 7B, a tensile force is applied to this assembly 50 in the axis direction and, therefore, the assembly 50a extended by a length Z compared with being in the natural length conditions is formed. At this time, the length Z is an amount satisfying the condition that the amount of contraction Y of the pliable tube 15 during high-pressure steam sterilization $\geq X1$ ($\geq X2$, $\geq X3$), and is the value larger than at least Y.

As shown in FIG. 7C, a molten resin for forming the integument layer 39 is extruded while the extended assembly 50a is a core material and, therefore, this assembly 50a is covered with the resin. Subsequently, the resin is held until curing is completed. By curing the resin, a desired pliable tube 15 is formed in which the assembly 50 extended by z compared with being in the natural length conditions is covered with the integument layer 39.

Regarding the step later than that shown in FIG. 7B, the pliable tube 15 may be formed by applying a covering of the tube element made of the resin which becomes the integument layer 39 to the assembly 50a of the aforementioned helical tube 37 and mesh-shaped tube 38.

Furthermore, when a covering of the integument layer 39 is applied, the assembly 50 composed of the aforementioned helical tube 37 and mesh-shaped tube 38 may be kept in the condition of being extended by a predetermined amount compared with being in the natural length conditions by applying a tensile force in the axis direction, a covering of the integument layer 39 may be applied by extrusion and, therefore, the pliable tube 15 may be formed.

As the resin constituting the aforementioned integument layer 39, it is better to select a resin satisfying the usage conditions from an amide-based thermoplastic elastomer, styrene-based resin, fluorine-based rubber, silicon-based rubber or a resin material made by blending them.

Regarding the pliable tube 15, gas supply tube 43, water supply tube 44, and endo-therapy product tube 45, speeds of contraction may vary depending on the materials, structures, and manufacturing methods therefor. Consequently, it is desirable that regarding the pliable tube 15, gas supply tube 43, water supply tube 44, and endo-therapy product tube 45, respective initial dimensions, materials, structures, and manufacturing methods are selected based on the amounts of contraction when loads are applied up to the endurance examples limit of the endoscope 2 against high-pressure steam sterilization.

In the present embodiment, only the pliable tube 15 constituting the insertion portion 7 is described. However, similar configuration may be adopted regarding the pliable tube constituting the universal cord 9 and a gas supply tube, water supply tube, and suction tube, although not shown in the drawing, installed therein.

Actions when the endoscope 2 configured as described above is subjected to high-pressure steam sterilization will be described.

First, typical conditions for high-pressure steam sterilization will be described.

Regarding the typical conditions, in the US standard ANSI/AAMI ST37-1992 approved by American National Standards Institute and issued by Association for the Advancement of Medical Instrumentation, the sterilization step is specified to be at 132° C. for 4 minutes in prevacuum type, and the sterilization step is specified to be at 132° C. for 10 minutes in gravity type.

Although the temperature condition during the sterilization step of high-pressure steam sterilization varies depending on the form of high-pressure steam sterilization apparatuses and the time of the sterilization step, in general, it is set within the range on the order of 115° C. to 138° C. Some sterilization apparatuses can be set at on the order of 142° C.

The time condition varies depending on the temperature condition during the sterilization step. In general, it is set at on the order of 3 to 60 minutes. Some sorts of sterilization apparatuses can be set at on the order of 100 minutes.

The pressure in a sterilization chamber during this step is generally set at on the order of +0.2 MPa relative to atmospheric pressure.

Next, the high-pressure steam sterilization step of the endoscope in general prevacuum type will be described briefly.

The endoscope 2, which is a target apparatus for sterilization and in which the waterproof cap 33 is fitted to the electric connector portion 11, is contained in the container case 34 for sterilization, and is placed in the sterilization chamber. By fitting the waterproof cap 33 to the aforementioned electric connector portion 11, the pressure control valve becomes in the condition of being closed and, therefore, the aforementioned vent holes are blocked. That is, the inside of the endoscope 2 and the outside are closed with watertightness. Subsequently, the inside of the sterilization chamber before the high-pressure steam sterilization step is made to be in the condition of reduced pressure (prevacuum step).

This prevacuum step is a step for making steam penetrate into detail of the target apparatus for sterilization during the sterilization step, and by reducing the pressure in the sterilization chamber, high-pressure high-temperature steam goes throughout the target apparatus for sterilization. In general, the pressure in the sterilization chamber during this prevacuum step is set at on the order of −0.07 to −0.09 MPa relative to atmospheric pressure.

However, when the pressure in the sterilization chamber is reduced during the prevacuum step, the external pressure becomes lower than the internal pressure of the endoscope 2 and, therefore, pressure difference occurs. Then, the pressure control valve of the aforementioned waterproof cap 33 is opened and, therefore, the inside of the endoscope 2 and the outside become in the condition of being communicated with the aforementioned vent holes therebetween. According to this, occurrence of a large pressure difference is prevented. That is, it is prevented that the endoscope 2 is broken due to the pressure difference between the internal pressure and the external pressure.

Subsequently, high-pressure high-temperature steam is supplied into the sterilization chamber and, therefore, sterilization is performed (sterilization step).

In this sterilization step, the inside of the sterilization chamber is pressurized. Then, such a pressure difference that the external pressure becomes higher than the internal pressure of the endoscope 2 occurs. Consequently, the pressure control valve of the aforementioned waterproof cap 33 is closed and, therefore, penetration of high-pressure steam into the inside of the endoscope through the vent holes is interrupted.

However, the high-pressure steam passes through the integument layer 39 of the aforementioned pliable tube 15 formed from a macromolecular material, an O-ring which is a seal device installed at the joint portion of the outer sheath material of the endoscope 2 and which is formed from fluororubber, silicon rubber, etc., and the like and, therefore, gradually penetrates into the inside of the endoscope.

At this time, the outer sheath material of the endoscope 2 becomes in the condition that a pressure has been generated, in which the pressure reduced in the prevacuum step and the pressure increased in the sterilization step are added and which trends from the outside toward the inside.

Subsequently, after the sterilization step is completed, in order to dry the target apparatus for sterilization after sterilization, the inside of the sterilization chamber is made to be in the reduced pressure condition again and, therefore, drying (drying step) is performed. In this drying step, the pressure in the sterilization chamber is reduced, the steam is removed from the inside of the sterilization chamber and, therefore, drying of the target apparatus for sterilization in the sterilization chamber is accelerated. In general, the pressure in the sterilization chamber during this drying step is set at on the order of −0.07 MPa to −0.09 MPa relative to atmospheric pressure. The aforementioned drying step is performed arbitrarily if necessary.

In the pressure reduction step after the sterilization step, the pressure in the sterilization chamber is reduced, the external pressure becomes lower than the internal pressure of the endoscope 2 and, therefore, pressure difference occurs. When this pressure difference occurs, at nearly the same time, the pressure control valve of the aforementioned waterproof cap 33 is opened and, therefore, the inside of the endoscope 2 and the outside become in the condition of being communicated with the vent holes therebetween. According to this, occurrence of a large pressure difference between the inside of the endoscope and the outside is prevented. When the pressure reduction step is completed, the inside of the sterilization chamber is pressurized and, therefore, such a pressure difference that the external pressure becomes higher than the internal pressure of the endoscope 2 occurs, the pressure control valve of the aforementioned waterproof cap 33 is closed.

When all steps of high-pressure steam sterilization are completed, the outer sheath material of the endoscope 2 becomes in the condition that a pressure, which is the pressure reduced in the pressure reduction step and which trends from the outside toward the inside, has been generated. Thereafter, by removing the waterproof cap 33 from the electric connector portion 11, the inside of the endoscope 2 and the outside are communicated through the aforementioned vent holes and, therefore, the inside of the endoscope 2 becomes at atmospheric pressure, and the load due to the pressure difference which has been brought about in the outer sheath material of the endoscope 2 is eliminated.

When the endoscope 2 configured as described above is sterilized repeatedly by high-pressure steam sterilization, the gas supply tube 43, water supply tube 44, and endo-therapy product tube 45 contract by X1, X2, and X3, respectively, due to thermal loads.

On the other hand, when the thermal load of high-pressure steam sterilization is applied to the aforementioned pliable tube 15, the temperature of the integument layer 39 becomes equivalent to or more than the thermal deformation temperature and, therefore, it becomes possible to thermally deform. Consequently, as shown in FIG. 7D, the pliable tube 15 is deformed in the direction of contraction of the integument layer 39 and, in addition, the helical tube 37 and the mesh-shaped tube 38 are also deformed in the direction of contraction. At this time, since the helical tube 37 and the mesh-shaped tube 38 are incorporated while being extended by Z ($\geqq$Y) compared with being in the natural length conditions, the aforementioned pliable tube 15 contracts by Y as a whole.

Since the relationships Y$\geqq$X1, Y$\geqq$X2, and Y$\geqq$X3 are set between respective amounts of contraction X1, X2, and X3 of these tubes 43, 44, and 45 and the amount of contraction Y of the pliable tube 15, even when the tubes 43, 44, and 45 contract, the aforementioned pliable tube 15 contracts by an amount equivalent to or more than those of the tubes 43, 44, and 45. Consequently, it is prevented that the length dimensions of the aforementioned gas supply tube 43, water supply tube 44, and endo-therapy product tube 45 become relatively small relative to the pliable tube 15 fixed indirectly and, therefore, the tubes become always in the condition of being sagged.

As described above, by setting the predetermined relationship between the amount of contraction of the pliable tube and the amounts of contraction of the tubes installed while being inserted through the insertion portion, when high-pressure steam sterilization is performed repeatedly, the tubes installed while being inserted through the insertion portion can be prevented from being pulled.

According to this, problems in that excessive forces are applied to the joint portions fixing end portions of these tubes, tubes are broken due to fatigue, inconvenience occurs in the shape of the curved portion during curving operation, the amount of control force is increased, and the like are overcome.

Since it can be prevented that the amounts of sagging of the gas supply tube 43, water supply tube 44, and endo-therapy product tube 45 relative to the pliable tube fixed indirectly become smaller than predetermined values, in curving operation or in the condition that the pliable tube is curved, these gas supply tube 43, water supply tube 44, and endo-therapy product tube 45 are moved freely in the pliable tube and, therefore, it is prevented that the light guide, electric cables, etc., are broken due to pressure.

According to these, durability of the built-in materials of the endoscope is improved and, in addition, operational ease of the endoscope is improved.

Furthermore, the pliable tube 15 may be formed as shown in FIG. 8A to FIG. 8D.

When the aforementioned pliable tube 15 is assembled, as shown in FIG. 8A, an assembly 50 is formed, in which the helical tube 37 and mesh-shaped tube 38 are combined. As shown in FIG. 8B, a molten resin for forming the integument layer 39 is extruded while this assembly 50 is a core material and, therefore, the assembly 50 is covered.

Subsequently, while the aforementioned integument layer 39 is cooled and is solidified completely, a tensile force is applied to the assembly 50 covered with the integument layer 39 in the axis direction, the assembly 50 is extended by Z ($\geq$Y) compared with being in the natural length conditions, and is held. According to this, by curing the integument layer 39, a desired pliable tube 15 is formed in which the assembly 50 extended by Z compared with being in the natural length conditions is covered with the integument layer 39 as shown in FIG. 8C.

When the thermal load of high-pressure steam sterilization is applied to the pliable tube 15 thus formed, the temperature of the integument layer 39 becomes equivalent to or more than the thermal deformation temperature and, therefore, it becomes possible to deform. Consequently, the helical tube 37, the mesh-shaped tube 38, and the integument layer 39, which have been incorporated while being extended compared with being in the natural length conditions, contract and, therefore, the pliable tube 15 contracts by Y as a whole.

By thus forming the pliable tube, when the pliable tube contracts, since the amount of contraction of the integument layer relative to the natural length conditions is small compared with that in the aforementioned method, a compressive stress applied to the inside of the integument layer can be reduced and, therefore, durability of the integument layer, that is, the pliable tube, can be improved.

Any one of or all of the aforementioned gas supply tube 43, water supply tube 44, and endo-therapy product tube 45 may be subjected to an annealing treatment in advance of assembling at a temperature at which a thermal road is similar to the thermal road in the high-pressure steam sterilization step and, therefore, may contract by a specified amount. According to this, the absolute values of the amounts of contraction X1, X2, and X3 become small, the range of the amount of contraction Y is increased and, therefore, flexibility in selection of the material, structure, and manufacturing method of the pliable tube 15 is increased. In addition, since the amount of contraction Y can also be reduced, the amount of change between at the initial condition and at high-pressure steam sterilization becomes small.

Contrary to the above description, the pliable tube 15 may be annealed in advance and, therefore, may contract by a specified amount within the range of the number of endurance examples of the endoscope 2 against high-pressure steam sterilization and within the range satisfying the relationships Y$\geq$X1, Y$\geq$X2, and Y$\geq$X3.

Next, an embodiment related to an endoscope, in which even when high-pressure steam sterilization is performed repeatedly, it is prevented that the inner diameter of the pliable tube is changed in the direction of contraction and inconvenience occurs in the built-in materials, that is, the inner diameter dimension remains in the condition as it is or becomes in the condition that the diameter is enlarged, will be described.

In the present embodiment, the pliable tube is formed in order that when the pliable tube 15 is applied with the thermal load during high-pressure steam sterilization and, thereafter, is returned to ambient temperature, the inner diameter becomes equivalent to or more than the inner diameter before application of the thermal load.

The configuration of a pliable tube according to the present embodiment will be described with reference to FIG. 9A and FIG. 9B which are diagrams for explaining the configuration of the pliable tube.

Regarding the pliable tube 15A according to the present embodiment, since the helical tube 37 and the mesh-shaped tube 38 are extended during the manufacturing step compared with being in the natural length conditions as described above, the inner diameter dimension has been reduced compared with that in the natural condition because of the structure thereof. That is, as shown in FIG. 9A and FIG. 9B, in the pliable tube formation conditions, the aforementioned helical tube 37 and the mesh-shaped tube 38 are integrated with the integument layer 39 while being in the condition that the diameter is reduced to $\phi$d (FIG. 9B) smaller than $\phi$D (FIG. 9A) which is the inner diameter in the natural length conditions, and that condition is maintained and fixed.

Consequently, when the thermal load of high-pressure steam sterilization is applied to the pliable tube 15, the temperature of the integument layer 39 becomes equivalent to or more than the thermal deformation temperature and, therefore, it becomes possible to deform. Regarding this sterilization step of high-pressure steam sterilization, a pressure of about 0.2 MPa is applied in the gravity type sterilization apparatus and a pressure of about 0.3 MPa is applied in the prevacuum type sterilization apparatus from the external side to the internal side of the pliable tube 15 and, therefore, a force is exerted in the direction of diameter reduction of the aforementioned pliable tube 15.

However, in the helical tube 37 and mesh-shaped tube 38 incorporated while the diameters have been reduced relative to the natural condition, since the force in the direction of diameter increase, which is a force tending to return to the natural condition, is always exerted, this force opposes the aforementioned force in the direction of diameter reduction and, therefore, the inner diameter is not reduced by a large degree in the aforementioned pressurized condition. In addition, when the aforementioned pressurized condition is completed, only the force in the direction of diameter increase is exerted on the helical tube 37 and mesh-shaped tube 38, and when the pliable tube 15 is cooled, the integument layer 39 becomes unable to deform. That is, the helical tube 37, mesh-shaped tube 38, and the integument layer 39 are fixed while being in this condition.

At this time, the inner diameters of the helical tube 37 and mesh-shaped tube 38 are kept and fixed to be equivalent to or more than the inner diameter before application of the thermal load of the high-pressure steam sterilization step although these vary depending on the cooling speed of the aforementioned integument layer 39. Consequently, the inner diameter dimension of the pliable tube 15 at ambient temperature after application of the thermal load of the high-pressure steam sterilization step becomes equivalent to or more than the inner diameter dimension at ambient temperature before application of the thermal load.

In the case of a prevacuum type sterilization step, since the pressure in the endoscope is generally kept in the condition of reduced pressure on the order of −0.09 MPa when the step is completed, it is desirable that the pliable tube 15 is formed while the diameters of the helical tube 37 and mesh-shaped tube 38 are reduced in order that a force of about 0.09 MPa or more is exerted on the helical tube 37 and mesh-shaped tube 38 in the direction of diameter increase.

Furthermore, in consideration of deformation in the pressurized condition, it is most reliable that the pliable tube 15 is formed in order that a force of +0.2 MPa during pressuring in the gravity type or about 0.29 MPa (0.2+0.09) or more in the prevacuum type in consideration of pressure difference between during pressuring and during pressure reduction is exerted in the direction of diameter increase.

As described above, by extending the helical tube and mesh-shaped tube compared with being in the natural length conditions in advance during the manufacturing step, since these helical tube and mesh-shaped tube are incorporated while the diameters are reduced relative to that in the natural condition, a force is always exerted in the direction of diameter increase during high-pressure steam sterilization and, therefore, it is prevented with reliability that the inner diameter of the pliable tube becomes equivalent to or less than the inner diameter dimension at ambient temperature.

According to this, when high-pressure steam sterilization is performed repeatedly, it is prevented that the inner diameter of the pliable tube is reduced and, therefore, the built-in light guide, electric cables, and pipeline tubes are broken due to pressure.

Since an increase in filling factor of the built-in materials in the insertion portion is prevented, a proper clearance is kept and, therefore, the built-in materials can move freely in the insertion portion.

According to these, it is prevented that the inner diameter dimension of the pliable tube contracts and the built-in materials are broken, and consequently, an endoscope having excellent durability is provided.

Furthermore, regarding the pliable tube according to the aforementioned embodiment shown in FIG. 8A to FIG. 8D, in the pliable tube formation conditions, the integument layer, in addition to the aforementioned helical tube and mesh-shaped tube, is extended compared with being in the natural length conditions, the inner diameter of the integument layer is also in the condition of being reduced compared with the inner diameter in the natural condition and, therefore, similar actions and effects are achieved.

Figure 10A:
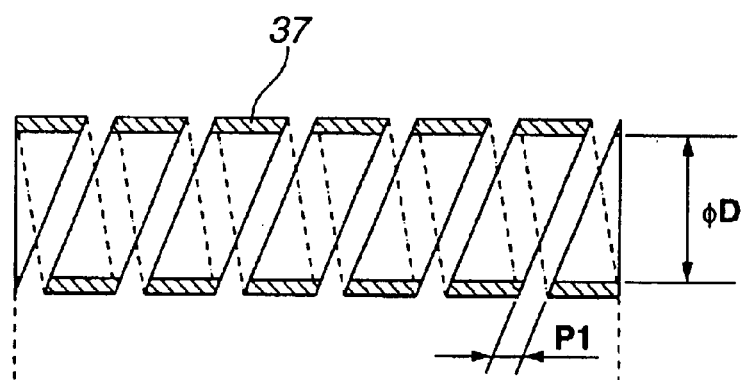
FIG. 10A and FIG. 10B are sectional views for explaining another configuration of a pliable tube according to an embodiment of the present invention.
Figure 10B:
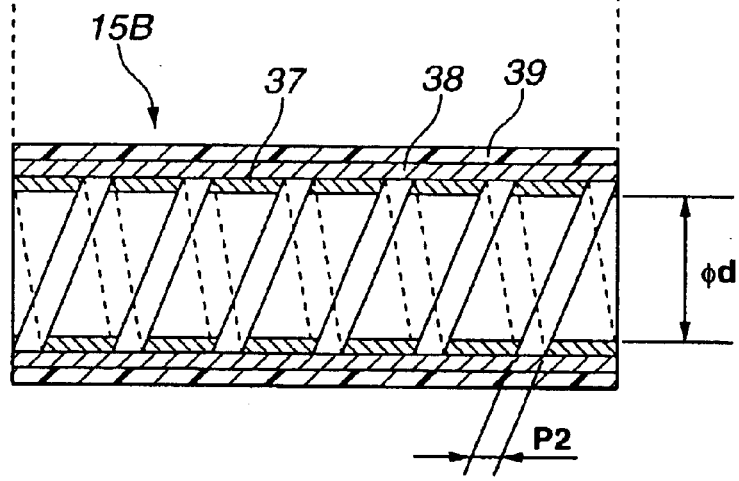

In the pliable tube formation conditions, the aforementioned helical tube 37 may be configured to be the same as in the natural length conditions as shown in FIG. 10A and FIG. 10B which are diagrams for explaining another configuration of the pliable tube. Specifically, the pliable tube 15B according to the present embodiment has a configuration in which in order that the length dimension is set to be the same as that in the natural length conditions, the interval P1 between the adjacent strips is specified to be P2 narrower than the interval in the natural condition and, in addition, the helical tube 37, in which the inner diameter dimension has been reduced to $\phi d$ smaller than the inner diameter $\phi D$ in the natural condition, is covered with the mesh-shaped tube 38 and the integument layer 39.

By thus configuring the pliable tube 15B, when the thermal load of high-pressure steam sterilization is applied, the temperature of the integument layer 39 becomes equivalent to or more than the thermal deformation temperature and, therefore, it becomes possible to deform. Consequently, an action tending to return to the natural condition is exerted on the helical tube 37. According to this, the inner diameter dimension of the pliable tube 15 at ambient temperature after application of the thermal load of the high-pressure steam sterilization step becomes equivalent to or more than the inner diameter dimension at ambient temperature before application of the thermal load. However, at this time, the interval between the adjacent strips is increased and, therefore, the total length is not changed.

Figure 9A:
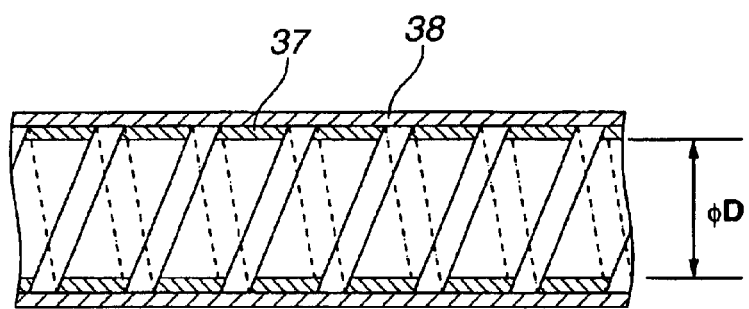
FIG. 9A and FIG. 9B are sectional views for explaining the configuration of a pliable tube according to an embodiment of the present invention.
Figure 9B:
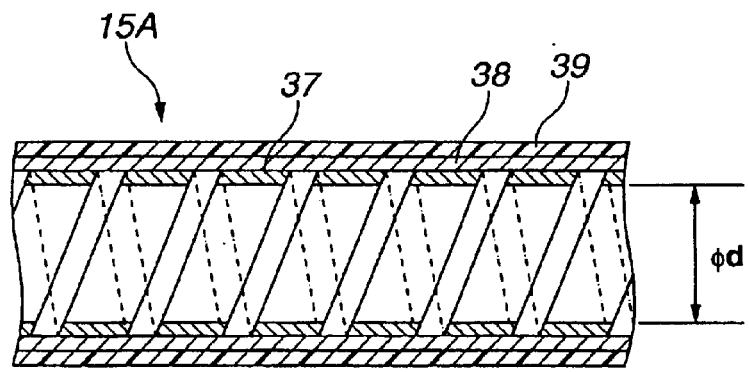

As described above, since the diameter of the helical tube is reduced and the interval between the strips is configured to be a narrow width, in addition to the effects of the pliable tube shown in the aforementioned FIG. 9A and FIG. 9B, it can be eliminated that the length of the pliable tube contracts due to high-pressure steam sterilization.

Furthermore, in a manner similar to that in the aforementioned helical tube, when the length of the mesh-shaped tube is not changed from that in the natural length conditions, the interval between adjacent knitted thin wires is specified to be smaller than that in the natural length conditions, and, therefore, the pliable tube is configured while the inner diameter is in the condition of being shrunken compared with that in the natural condition, similar actions and effects can also be achieved.

The aforementioned configuration may be used for a multilayer helical tube configured by combining helical tubes doubly or triply.

As described above, according to the present invention, the endoscope, in which the inconvenience brought about due to contraction of the tube element built in the insertion portion during high-pressure steam sterilization is prevented, is provided.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising a pliable tube composed of an integument layer formed from a resin and a metal tube integrally fitted into this integument layer in an insertion portion of the endoscope, wherein the inner diameter dimension of the pliable tube at ambient temperature after application of a thermal load of high-pressure steam sterilization is larger than the inner diameter dimension at ambient temperature before application of the thermal load.

2. The endoscope according to claim 1, wherein the integument layer is formed from a resin having a thermal deformation temperature equivalent to or less than a temperature applied during a high-pressure steam sterilization, and the metal tube is formed under a pliable tube formation condition while the diameter of the metal tube is reduced compared with that in a natural condition.

3. The endoscope according to claim 1, wherein:

the metal tube comprises a helical tube formed from a metal strip and a mesh-shaped tube formed from a thin metal wire; and the diameter of at least one of the helical tube and the mesh-shaped tube is reduced in a pliable tube formation condition compared with that in a natural condition.

4. The endoscope according to claim 1,
wherein the diameter of the integument layer is reduced in a pliable tube formation condition in order that a predetermined force is exerted in the direction of diameter increase in a natural condition.

5. The endoscope according to claim 1,
wherein the metal tube is formed in order that a predetermined force is exerted in the direction of diameter increase in a diameter reduction condition.

6. The endoscope according to claim 1,
wherein the maximum temperature in the high-pressure steam sterilization step is within the range of about 115° C. to 140° C.

7. The endoscope according to claim 1,
wherein the integument layer of the pliable tube is formed from any one of ester-based thermoplastic elastomer, amide-based thermoplastic elastomer, styrene-based resin, fluorine-based rubber, and silicon-based rubber, or a resin member made by blending them.

8. The endoscope according to claim 1,
wherein the diameter of the metal tube is reduced in order that a force not less than a pressure difference between an inside and an outside of the pliable tube due to the high-pressure steam sterilization is exerted in a direction of diameter increase.

9. The endoscope according to claim 8,
wherein the diameter of the metal tube is reduced in order that a force not less than 0.09 MPa is exerted in the direction of diameter increase.

10. The endoscope according to claim 9,
wherein the diameter of the metal tube is reduced in order that a force not less than 0.29 MPa is exerted in the direction of diameter increase.

* * * * *